(12) United States Patent
Deshpande et al.

(10) Patent No.: US 12,374,425 B2
(45) Date of Patent: Jul. 29, 2025

(54) RAPID DETECTION OF GENE FUSIONS

(71) Applicant: Illumina, Inc., San Diego, CA (US)

(72) Inventors: Viraj Deshpande, San Diego, CA (US); Johann Felix Wilhelm Schlesinger, San Diego, CA (US); Sean Truong, San Diego, CA (US); John Cooper Roddey, San Diego, CA (US); Michael Ruehle, Fort Worth, TX (US); Severine Catreux, San Diego, CA (US); Rami Mehio, San Diego, CA (US)

(73) Assignee: Illumina, Inc., San Diego, CA (US)

(*) Notice: Subject to any disclaimer, the term of this patent is extended or adjusted under 35 U.S.C. 154(b) by 480 days.

(21) Appl. No.: 17/112,956

(22) Filed: Dec. 4, 2020

(65) Prior Publication Data

US 2021/0193254 A1 Jun. 24, 2021

Related U.S. Application Data

(60) Provisional application No. 62/944,304, filed on Dec. 5, 2019.

(51) Int. Cl.
*G16B 30/00* (2019.01)
*G06F 18/25* (2023.01)
(Continued)

(52) U.S. Cl.
CPC ........... *G16B 30/00* (2019.02); *G06F 18/251* (2023.01); *G06N 20/00* (2019.01); *G16B 20/00* (2019.02); *G16B 30/10* (2019.02)

(58) Field of Classification Search
CPC ...... G06F 18/251; G06N 20/00; G16B 20/00; G16B 30/10
See application file for complete search history.

(56) References Cited

U.S. PATENT DOCUMENTS

| 10,354,747 | B1 | 7/2019 | Depriso et al. |
| 2016/0019340 | A1 | 1/2016 | Gottimukkala et al. |

(Continued)

FOREIGN PATENT DOCUMENTS

| CN | 107267646 A | 10/2017 |
| CN | 110168647 A | 8/2019 |

(Continued)

OTHER PUBLICATIONS

Schatz, M.C., Trapnell, C., Delcher, A.L. et al. High-throughput sequence alignment using Graphics Processing Units. BMC Bioinformatics 8, 474 (2007). https://doi.org/10.1186/1471-2105-8-474 (Year: 2007).*

(Continued)

*Primary Examiner* — Karlheinz R. Skowronek
*Assistant Examiner* — Emilie A Neulen
(74) *Attorney, Agent, or Firm* — Illumina, Inc.

(57) ABSTRACT

Methods, systems, and apparatuses, including computer programs for identifying a gene fusion in a biological sample are disclosed. The method can include actions of obtaining first data that represents a plurality of aligned reads, identifying a plurality of fusion candidates included within the obtained first data, filtering the plurality of fusion candidates to determine a filtered set of fusion candidates, for each particular fusion candidate of the filtered set of fusion candidates: generating, by one or more computers, input data for input to a machine learning model that includes extracted feature data that to represents the particular fusion candidate, providing the generated input data as an input to the machine learning model that has been trained to generate output data representing a likelihood that a fusion candidate is a valid gene fusion, and determining whether the particular fusion candidate corresponds to a valid gone fusion based on the output data.

31 Claims, 4 Drawing Sheets

(51) Int. Cl.
  *G06N 20/00* (2019.01)
  *G16B 20/00* (2019.01)
  *G16B 30/10* (2019.01)

(56) References Cited

U.S. PATENT DOCUMENTS

| | | |
|---|---|---|
| 2018/0341746 A1 | 11/2018 | Mao et al. |
| 2018/0355423 A1 | 12/2018 | Yang et al. |
| 2020/0105373 A1* | 4/2020 | Zheng ............... C12Q 1/6827 |

FOREIGN PATENT DOCUMENTS

| | | | |
|---|---|---|---|
| CN | 110322925 A | 10/2019 | |
| RU | 2016149233 | 6/2018 | |
| RU | 2704286 | 10/2019 | |
| WO | WO-2016055971 A2 * | 4/2016 | ............ G16B 20/00 |
| WO | WO-2020113237 A1 * | 6/2020 | ........... A61B 5/4836 |

OTHER PUBLICATIONS

Langmead, B. A tandem simulation framework for predicting mapping quality. Genome Biol 18, 152 (2017). https://doi.org/10.1186/s13059-017-1290-3 (Year: 2017).*

PCT International Preliminary Report on Patentability in International Appln. No. PCT/US2020/063496, dated May 17, 2022, 10 pages.

Abate, F. et al., "Pegasus: a comprehensive annotation and prediction tool for detection of driver gene fusions in cancer", BMC Syst Biol doi: 10.1186/s12918-014-0097-z., Sep. 4, 2014, 1-30.

McPherson, A. et al., "deFuse: An Algorithm for Gene Fusion Discovery in Tumor RNA-Seq Data", PLoS Comput Biol. 7(5): e1001138., May 19, 2011, 1-30.

PCT/US2020/063496 , "International Search Report and Written Opinion", Mar. 22, 2021, 1-17.

RU Office Action in Russian Appln. No. 2021125284, dated Aug. 4, 2023, 6 pages (with English translation).

RU Office Action in Russian Appln. No. 2021125284, dated Jan. 20, 2023, 16 pages (with English translation).

CN Office Action in Chinese Appln. No. 202080021779.9, mailed on Dec. 16, 2023, 16 pages (with English translation).

CN Office Action in Chinese Appln. No. 2020800217799.9 mailed on November 1, No. 202080021779.9 2024, 9 pages (with English translation).

JP Office Action in Japanese Appln. No. 2021-557678, mailed on Sep. 9, 2024, 10 pages (with English translation).

* cited by examiner

RAPID DETECTION OF GENE FUSIONS

CROSS-REFERENCE TO RELATED APPLICATION

This application claims the benefit of U.S. Provisional Patent Application No. 62/944,304, filed on Dec. 5, 2019, which is incorporated herein by reference in its entirety.

BACKGROUND

Gene fusions can be used as oncogenic drivers that important diagnostic and therapeutic targets in treatment of diseases such as cancer.

SUMMARY

According to one innovative aspect of the present disclosure, a computer-implemented method for identifying one or more gene fusions in a biological sample is disclosed. In one aspect, method can include actions of obtaining, by one or more computers, first data that represents a plurality of aligned reads from a read alignment unit, identifying, by one or more computers, a plurality of gene fusion candidates included within the obtained first data, filtering, by one or more computers, the plurality of gene fusion candidates to determine a filtered set of gene fusion candidates, for each particular gene fusion candidate of the filtered set of gene fusion candidates: generating, by one or more computers, input data for input to a machine learning model, wherein generating the input data comprises extracting feature data to represent the particular gene fusion candidate from data that includes: (i) one or more segments of a reference sequence to which the particular gene fusion candidate was aligned by the read alignment unit, and (ii) data generated based on output of the read alignment unit, providing, by one or more computers, the generated input data as an input to the machine learning model, wherein the machine learning model has been trained to generate output data representing a likelihood that a gene fusion candidate is a valid gene fusion based on the machine learning model processing input data representing (i) one or more segments of a reference sequence to which the particular gene fusion candidate was aligned to by the read alignment unit, and (ii) data generated based on output of the read alignment unit, obtaining, by one or more computers, output data generated by the machine learning model based on the machine learning model processing the generated input data, and determining, by one or more computers, whether the particular fusion candidate corresponds to a valid gene fusion candidate based on the output data.

Other versions include corresponding systems, apparatus, and computer programs to perform the actions of methods defined by instructions encoded on computer readable storage devices.

These and other versions may optionally include one or more of the following features. For instance, in some implementations, generating the input data further comprises extracting feature data that includes annotation data describing annotations of the segments of the reference sequence to which the particular gene fusion candidate was aligned to by the read alignment unit. In such implementations, the machine learning model has been trained to generate output data representing a likelihood that a gene fusion candidate is a valid gene fusion candidate based on the machine learning model processing input data representing: (i) one or more segments of a reference sequence to which the particular gene fusion candidate was aligned to by the read alignment unit, (ii) annotation data describing annotations of the segments of the reference sequence to which the particular gene fusion candidate was aligned to by the read alignment unit, and (iii) data generated based on output of the read alignment unit.

In some implementations, identifying, by one or more computers, a plurality of gene fusion candidates included within the obtained first data can include identifying, by one or more computers, a plurality of split-read alignments.

In some implementations, identifying, by one or more computers, a plurality of gene fusion candidates included within the obtained first data comprises identifying, by one or more computers, a plurality of discordant read pair alignments.

In some implementations, the read alignment unit is implemented using a set of one or more processing engines that are configured using hardware logic circuits that have been physically arranged to perform operations, using the hardware logic circuits, to: (i) receive data representing a first read, (ii) map the data representing the first read to one or more portions of a reference sequence to identify one or more matching reference sequence locations, (iii) generate one or more alignment scores corresponding to each of the matching reference sequence locations for the first read, (iv) select one or more candidate alignments for the first read based on the one or more alignment scores, and (v) output data representing a candidate alignment for the first read.

In some implementations, the read alignment unit is implemented using a set of one or more processing engines by using one or more central processing units (CPUs) or one or one or more graphics processing units (GPUs) to execute software instructions that cause the one or more CPUs or one or more GPUS to: (i) receive data representing a first read, (ii) map the data representing the first read to one or more portions of a reference sequence to identify one or more matching reference sequence locations for the first read, (iii) generate one or more alignment scores corresponding to each of the matching reference sequence locations for the first read, (iv) select one or more candidate alignments for the first read based on the one or more alignment scores, and (v) output data representing a candidate alignment for the first read.

In some implementations, method can further include receiving, by the read alignment unit, a plurality of reads that are not yet aligned, aligning, by the read alignment unit, a first subset of the plurality of reads, and storing, by the read alignment unit, the first subset of aligned reads in a memory device. In such implementations, obtaining, by one or more computers, first data that represents a plurality of aligned reads from a read alignment unit can include obtaining, by one or more computers, the first subset of aligned reads from the memory device and performing one or more of the operations of claim 1 while the read alignment unit aligns a second subset of the plurality of reads that are not yet aligned.

In some implementations, the data generated based on the output of the read alignment unit can include any one or more of a variant allele frequency count, a count of unique read alignments, a read coverage across the transcript, a MAPQ score, or data that indicates a homology between parent genes.

In some implementations, determining whether the particular fusion candidate corresponds to a valid gene fusion candidate based on the output data can include determining, by one or more computers, whether the output data satisfies a predetermined threshold, and based on determining that the output data satisfies the predetermined thresholds, determining that the particular fusion candidate corresponds to a valid gene fusion candidate.

In some implementations, determining whether the particular fusion candidate corresponds to a valid gene fusion candidate based on the output data can include: determining, by one or more computers, whether the output data satisfies a predetermined threshold, and based on determining that the output data does not satisfy the predetermined thresholds, determining that the particular fusion candidate does not correspond to a valid gene fusion candidate.

These and other innovative aspects of the present disclosure are readily apparent in view of the detailed description, the accompanying drawings, and the claims.

DETAILED DESCRIPTION

The present disclosure is directed to systems, methods, apparatuses, computer programs, or any combination thereof, for rapidly detecting gene fusions. The presence of certain gene fusions can be important indicators of a particular disease, an indicator that suggests use of a particular therapeutic for a particular disease, or a combination thereof. For example, certain gene fusions can be indicators of a particular type of cancer, for example, e.g., acute and chronic myeloid leukemias, myelodysplastic syndromes (MDS), soft tissue sarcomas, or treatments therefor. The present disclosure can rapidly detect accurate gene fusions by using a filtering engine to reduce a number of gene fusion candidates (also referred to here as "fusion candidates") processed to determine whether each fusion candidate is a valid gene fusion. This filtering engine enables high-accuracy selection of fusions candidates for subsequent analysis while also achieving a reduction in computational resources that need to be expended to identify valid gene fusions, as only the filtered subset of candidate gene fusions can be advanced for further downstream processing as described herein.

The reduced candidate gene fusion set also provides other technological advantages. For example, the presently disclosed methods and systems provide a reduced runtime compared to conventional methods that process and score all gene fusion candidates. Reduced runtime to perform its operations also directly results in a reduction in the expenditure of processing resources (e.g., CPU or GPU resources), memory usage, and power consumption. While a filtering engine provides a reduced runtime compared to conventional methods, the presently disclosed methods and systems can also provide other ways to reduce runtime. For example, in some implementations, even further reductions in runtime can be achieved by using a hardware-accelerated read alignment unit to perform mapping, aligning, and generation of metadata used to process the candidate gene fusions.

Figure 1:
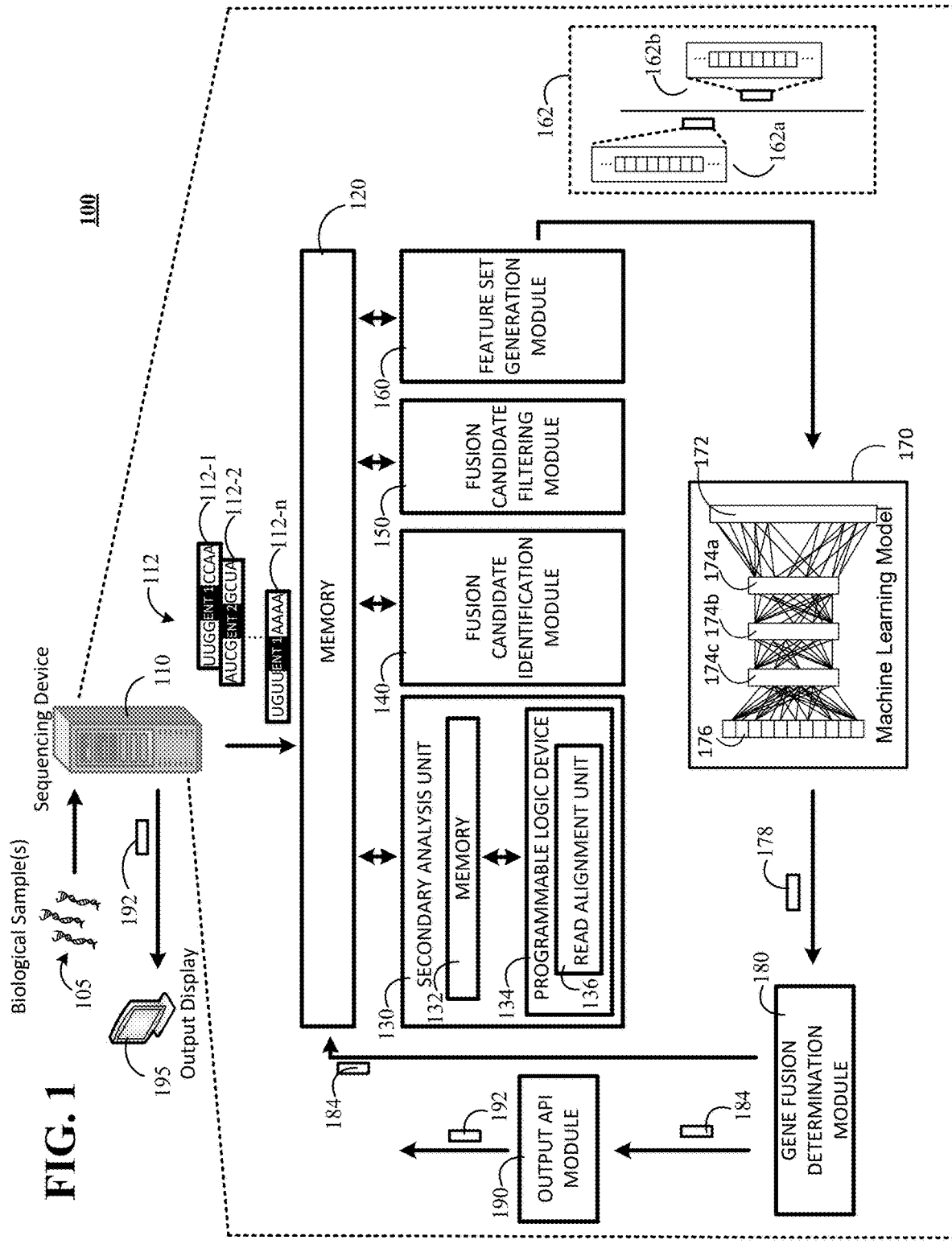
FIG. 1 is a block diagram of an example of a system for rapid detection of valid gene fusions.

FIG. 1 is a block diagram of an example of a system 100 for rapid detection of valid gene fusions. The system 100 can include a nucleic acid sequencing device 110, a memory 120, a secondary analysis unit 130, a fusion candidate identification module 140, a fusion candidate filtering module 150, a feature set generation module 160, a machine learning model 170, a gene fusion determination module 180, an output application program interface (API) module 190, and an output display 195. In the example of FIG. 1, each of these components is described as being implemented within the nucleic acid sequencing device 110. However, the present disclosure is not limited to such embodiments.

Instead, in some implementations, one or more of the components described in FIG. 1 can be executed on a computer outside the nucleic acid sequencing device 110. For example, in some implementations, the secondary analysis modules may be implemented within the nucleic acid sequencing device 110 and the fusion candidate identification module 140, a fusion candidate filtering module 150, a feature set generation module 160, a machine learning model 170, a gene fusion determination module 180, an output application program interface (API) module 190 can be implemented in one or more different computers. In such implementations, the one or more different computers and the nucleic acid sequencing device can be communicatively coupled using one or more wired networks, one or more wireless networks, or a combination thereof.

For purposes of this specification, the term "module" includes one or more software components, one or more hardware components, or any combination thereof, which can be used to realize the functionality attributed to a respective module by this specification. In general, a "module," as described herein, uses one or more processors to execute software instructions to realize the functionality of the module described herein. A processor can include a central processing unit (CPU), graphics processing unit (GPU), or the like.

Likewise, the term "unit" as used in this specification includes one or more software components, one or more hardware components, or any combination thereof, which can be used to realize the functionality attributed to a respective unit by this specification. In general, a "unit," as described herein, uses one or more hardware components such as hardwired digital logic gates or hardwired digital logic blocks arranged as processing engines to perform operations that realize the functionality of the unit described herein. Such hardwired digital logic gates or hardwired digital logic circuits can include a field programmable gate array (FPGA), an application specific integrated circuit (ASIC), or the like.

The nucleic acid sequencing device 110 (also referred to herein as sequencing device 110) is configured to perform primary nucleic acid sequence analysis. Performing primary analysis can include receiving, by the sequencing device 110, a biological sample 105 such as a blood sample, tissue sample, sputum, or nucleic acid sample and generating, by the sequencing device 110, output data such as one or more reads 112 that each represent an order of nucleotides of a nucleic acid sequence of the received biological sample. In some implementations, sequencing, by the nucleic acid sequencer 110, can be performed in multiple read cycles, with a first read cycle "Read 1" generating one or more first reads representing an order of nucleotides from a first end of a nucleic acid sequence fragment and a second read cycle "Read 2" generating one or more second reads, respectively, representing an order of nucleotides from the other ends of one of the nucleic acid sequence fragments. In some implementations, reads can be short reads of approximately 80 to 120 nucleotides in length. However, the present disclosure is not limited to reads of any particular nucleotide length. Instead, the present disclosure can be used for reads of any nucleotide length.

In some implementations, the biological sample 105 can include a DNA sample and the nucleic acid sequencer 110 can include a DNA sequencer. In such implementations, the order of sequenced nucleotides in a read generated by the nucleic acid sequencer can include one or more of guanine (G), cytosine (C), adenine (A), and thymine (T) in any combination. In some implementations, the nucleic acid sequencer 110 can be used to produce RNA reads of a biological sample 105. In such implementations, this can occur using RNA-seq protocols. By way of example, a biological sample 105 can be preprocessed using reverse-transcription to form complementary DNA (cDNA) using a reverse transcriptase enzyme. In other implementations, the nucleic acid sequencer 110 can include an RNA sequencer, and the biological sample can include an RNA sample. RNA reads produced using cDNA or via an RNA sequencer can comprised of C, G, A, and Uracil (U). The example of FIG. 1 described herein is described with reference to generation and analysis of RNA reads. However, the present disclosure can be used to produce and analyze any type of nucleic acid sequence reads including DNA or RNA reads.

The sequencing device 110 can include a next generation sequencer (NGS) that is configured to generate sequence reads such as reads 112-1, 112-2, 112-n, where "n" is any positive integer greater than 0, for a given sample in a manner that achieves ultra-high throughput, scalability, and speed through the use of massively parallel sequencing technology. The NGS enables rapid sequencing of whole genomes, the ability to zoom into deeply sequenced target regions, utilize RNA sequencing (RNA-Seq) to discover novel RNA variants and splice sites, or quantify mRNAs for gene expression analysis, analysis of epigenetic factors such as genome-wide DNA methylation and DNA-protein interactions, sequencing of cancer samples to study rare somatic variants and tumor subclones, and to study microbial diversity, e.g., in humans or in the environment.

The sequencing device 110 can sequence the biological sample 105 and generate a corresponding set of reads represented using A, C, T, and G. The sequencing device can then perform reverse-transcription to generate a cDNA sequence that represents the corresponding RNA sequence. These RNA sequence reads 112-1, 112-2, 112-n are output by the sequencing device 110 and stored in the memory device 120. In some implementations, the RNA sequence reads 112-1, 112-2, 112-n may be compressed into data records of smaller size prior to storage of the reads 112-1, 112-2, 112-n in the memory device 120. The memory device 120 can be accessible by each of the components of FIG. 1 including the secondary analysis unit 130, the fusion candidate identification module 140, the fusion candidate filtering module 150, the feature set generation module 160, the machine learning model 170, the gene fusion determination module 180, and the output API module 190. Though respective modules may be depicted as providing an output of a first module to a second module, practical implementation of such a feature may include the first module storing the output in a memory device such as memory 120 and the second module accessing the stored output from the memory device and processing the accessed output as an input to the second module.

The secondary analysis unit 130 can access the reads 112-1, 112-2, 112-n stored in the memory device 120 and perform one or more secondary analysis operations on the reads 112-1, 112-2, 112-n. In some implementations, the reads 112-1, 112-2, 112-n may be stored in the memory device 120 in compressed data records. In such implementations, the secondary analysis unit can perform decompression operations on the compressed read records prior to performing secondary analysis operations on the read records. Secondary analysis operations can include mapping one or more reads to a reference genome, aligning one or more reads to the reference genome, or both. In some implementations, secondary analysis operations can also include variant calling operations. In addition to performance of secondary analysis operations, the secondary analysis unit 130 can also be configured to perform sorting operations. Sorting operations can include, for example, ordering reads that have been aligned by the secondary analysis unit based on the position in the reference genome to which the aligned reads were mapped.

In some implementations, such as the example of FIG. 1, the secondary analysis unit 130 can include a memory 132 and a programmable logic device 134. The programmable logic device 134 can have hardware logic circuits that can be dynamically configured to include one or more secondary analysis operational units such as a read alignment unit 136 and can be used to perform one or more secondary analysis operations using the hardware logic circuits. Dynamically configuring the programmable logic device 134 to include a secondary analysis operational unit such as a read alignment unit 136 can include, for example, providing one or more instructions to the programmable logic device 134 that causes the programmable logic device 134 to arrange hardware logic gates of the programmable logic device 134 into a hardwired digital logic configuration that is configured to realize functionality, in hardware logic, of the read alignment unit 136.

The one or more operations that trigger dynamic configuration of the programmable logic device 134 can include compiled hardware description language code, one or more instructions for the programmable logic device 134 to configure itself based on the compiled hardware description language code, or the like. Such operations that trigger dynamic configuration of the programmable logic device 134 can be generated and deployed to the programmable logic device 134 by a control program executed by the sequencing device 110, or other computer hosting the control program. In some implementations, the control program can be a software module whose instructions reside in a memory device such as memory 120. The functionality of the control program to generate and deploy instructions hardware description language code or other instructions to configure the programmable logic device 134 can be realized by executing the control program software module using one or more processors such one or more CPUs or one or more GPUs.

The functionality of the read alignment unit 136 can include obtaining one or more first reads such as RNA reads 112-1, 112-2, 112-n that were stored in memory 120 by the sequencing device 110, mapping the obtained first reads 112-1, 112-2, 112-n to one or more reference sequence locations of a reference sequence, and then aligning the mapped first reads 112-1, 112-2, 112-n to reference sequence. That is, the mapping stage can identify a set of candidate reference sequence locations for each particular read of the obtained first reads that match the particular read. Then, the alignment stage can score each of the candidate reference sequence locations and select a particular reference sequence location having the highest alignment score as the correct alignment for the particular read. A reference sequence can include an organized series of nucleotides corresponding to a known genome.

Arranging hardware logic gates of the programmable logic device 134, responsive to the one or more instructions from the control program, can include configuring logic gates such as AND gates, OR gates, NOR gates, XOR gates, or any combination thereof, to execute digital logic functions of a read alignment unit 136. Alternatively, or in addition, arranging hardware logic gates can include dynamically configured logic blocks comprising customizable hardware logic units to perform complex computing operations including addition, multiplication, comparisons, or the like. The precise arrangement of the hardware logic gates, logic blocks, or a combination thereof, is defined by the instructions received from the control program. The received instructions can include, or be derived from, compiled hardware description language (HDL) program code that was written by an entity and defines the schematic layout of the secondary analysis operational unit that is to be programmed into the programmable logic device 134. The HDL program code can include program code written in a language such a Very High Speed Integrated Circuit Hardware Description Language (VHDL), Verilog, or the like. The entity can include one or more human users that drafted the HDL program code, one or more artificially intelligent agents that generated the HDL program code, or a combination thereof.

The programmable logic device 134 can include any type of programmable logic device. For example, the programmable logic device 134 can include one or more field programmable gate arrays (FPGAs), one or more complex programmable logic devices (CPLDs), or one or more programmable logic arrays (PLA), or a combination thereof, that are dynamically configurable and reconfigurable, as needed, by the control program to execute a particular workflow. For example, in some implementations, it may be desirable to use the programmable logic device 134 as a read alignment unit 136, as described above. However, in other implementations, it may be desirable to use the programmable logic device 134 to perform variant calling functions or functions in support of variant calling such as a Hidden Markov Model (HMM) unit. In yet other implementations, the programmable logic device 134 can also be dynamically configured to support general computing tasks such as compression and decompression, because the hardware logic of the programmable logic device 134 is capable of performing these tasks, and the other tasks identified above, much faster than the performance of the same tasks using software instructions executed by one or more processing units 150. In some implementations, the programmable logic device 134 can be dynamically reconfigured during runtime to perform different operations.

By way of example, in some implementations, the programmable logic device 134 can be implemented using an FPGA that be dynamically configured as a decompression unit to access data representing a compressed version of first reads 112-1, 112-2, 112-n stored in the memory device 120 or 132. The secondary analysis unit 130 can use the decompression unit to decompress the compressed data representing the first reads 112-1, 112-2, 122-n (e.g., if the reads received from the nucleic acid sequencer are compressed). The decompression unit can store decompressed reads in the memory 120 or 132. In such implementations, the FPGA can then be dynamically reconfigured as a read alignment unit 136 and used to perform mapping and aligning of the decompressed first reads 112-1, 112-2, 112-n now stored in the memory 132 or 120. The read alignment unit 136 can then store data representing the mapped and aligned reads in the memory 132 or 120. Though a series of operations is described as including decompression and mapping and aligning operations, the present disclosure is not limited to performing those operations or only those operations. Instead, the programmable logic device 134 can be dynamically configured to perform functionality of any operational unit in any order, as necessary, to realize the functionality described herein.

The example of FIG. 1 describes a secondary analysis unit 130 that uses a hardware logic device in the form of programmable logic device 134 to implement a read alignment unit 136. However, the present disclosure is not limited to using programmable logic devices to implement the read alignment unit 136. Instead, other types of integrated circuits can be used to implement a read alignment unit 136 in hardwired digital logic of the secondary analysis unit 130. For example, in some implementations, a secondary analysis unit 143 can be configured to use one or more Application-Specific Integrated Circuits (ASIC) to implement the functionality of one or more secondary analysis operational units. Though not reprogrammable, one or more ASICs can be designed with custom hardware logic of one or more secondary analysis operational units such as a read alignment unit 136, a variant calling unit, a variant calling computational support unit, or the like to accelerate and parallelize performance of secondary analysis operations. In some implementations, use of one or more ASICs as the hardwired logic circuits of the secondary analysis unit 130 that realizes functionality of one or more secondary analysis operations units can be even faster than using a programmable logic device such as an FPGA. Accordingly, a skilled artisan would understand that an ASIC could be used in place of a programmable logic device such as an FPGA in any of the embodiments described herein. For implementations where ASICs are to be employed, a dedicated ASIC or dedicated logic groups of a single ASIC would need to be employed for each secondary analysis operation unit that is to be performed by an ASIC. By way of example, one or more ASICs for read alignment, one or more ASICs for decompression, one or more ASICs for compression, or a combination thereof. Alternatively, the same functionality could also be achieved with dedicated logic groups within the same ASIC.

In addition, examples of the present disclosure discussed with reference to systems 100 and 300 of FIGS. 1 and 3, respectively, are described with reference to use of a hardware implementation of a read alignment unit 136 in a programmable logic device. In addition, it is indicated above that one or more ASICs can be used to implement the read alignment engine or other secondary analysis operation units. However, the present disclosure is not limited to use of a hardware units to implement such secondary analysis operations. Instead, in some implementations, the any of the operations described herein as being performed by the programmable logic device such as read alignment, compression, or decompression, can also be implemented using one or more software modules.

With reference to the example of FIG. 1, execution of the system 100 can begin with the sequencing device 110 sequencing the biological sample 105. Sequencing the biological sample can include generating, by the sequencing device 110, read sequences that are a data representation of the ordered sequences of nucleotides present in the biological sample 105. If the system 100 is configured to process DNA reads, then the reads generated by the sequencing device 110 can be stored in the memory 120.

Alternatively, in some implementations, if the system 100 is configured to process RNA reads, the sequencing device 110 can be configured to perform preprocessing of the biological sample 110 using reverse-transcription to form complementary DNA (cDNA) using a reverse transcriptase enzyme. In such implementations, such as the implementation in the example of FIG. 1, the reads generated by the sequencing device 110 include RNA reads 112-1, 112-2, 112-n. In other implementations, the nucleic acid sequencer 110 can include an RNA sequencer, and the biological sample can include an RNA sample. Regardless of whether the RNA reads are produced by a DNA sequencing device using cDNA or via an RNA sequencer, the RNA reads each include a sequence of nucleotides comprised of C, G, A, and U. The reads 112-1, 112-2, 112-n can be stored in the memory 120 in a compressed or uncompressed format.

Execution of the system 100 can continue with the secondary analysis unit 130 obtaining the reads 112-1, 112-2, 112-n stored in the memory 120. In some implementations, the secondary analysis unit 130 can access the reads 112-1, 112-2, 122-n in the memory device 120 and store the accessed reads 112-1, 112-2, 112-n into the memory 132 of the secondary analysis unit 130. In other implementations, upon a determination by a control program that sequencing of the reads 112-1, 112-2, 112-n has been completed and that the secondary analysis unit 130 is available to perform secondary analysis operations, the control program can load the reads 112-1, 112-2, 112-n into the memory 132 of the secondary analysis unit 130.

If reads 112-1, 112-2, 112-n are compressed, secondary analysis unit 130 can dynamically configure the programmable logic device 134 as a decompression unit in order to access the reads 112-1, 112-2, 112-n in the memory 132 or 120, decompress, the reads 112-1, 112-2, 112-n, and then store the decompressed reads 112-1, 112-2, 112-n in the memory 1320 or 120. In some implementations, the secondary analysis unit can dynamically reconfigure the programmable logic device and perform decompression responsive to instructions from a control program.

If the reads 112-1, 112-2, 122-n are not compressed, the secondary analysis unit 130 can access the reads from the memory 132 or 120 and perform read alignment operations. In some implementations, the secondary analysis unit 130 may receive an instruction from a control program that instructs the secondary analysis unit 130 to configure or reconfigure programmable logic device 134 to include a read alignment unit 136 and then use the read alignment unit 136 to perform alignment of the reads 112-1, 112-2, 112-n. Alternatively, in other implementations, the programmable logic device may already have been configured to include a read alignment unit 136 and use the read alignment unit 136 to perform alignment of the reads 112-1, 112-2, 112-n. In yet other implementations, the secondary analysis unit 130 may include an ASIC that is configured to perform read alignment and then use the ASIC to perform alignment of the reads 112-1, 112-2, 112-n.

The secondary analysis unit 130 can be configured to perform read alignment operations in parallel with gene fusion analysis. For example, the secondary analysis unit 140 can obtain a first batch of reads generated by the sequencing device 110 that are not aligned, use the read alignment unit 136 to align the first batch of reads, use a sorting engine which may be implemented in a hardware configuration of the programmed logic device 136 or a implemented in software by executing program instructions to sort the aligned reads, and then output the first batch of aligned and sorted reads for storage in a memory device 132, 130. In some implementations, the memory 132 can function as a local cache for the secondary analysis unit 132 that loads data that is to be processed by the read alignment unit and then offloads data that has been output by the read alignment unit 136. Thus, once the first batch of aligned reads has been output by the read alignment unit 136 to the memory 132, the first batch of aligned reads can be sorted and then be output to the memory 120. Then, the fusion candidate identification module 140 can access the first batch of aligned and sorted reads from the memory 120 and begin processing the first batch of aligned and sorted reads while the secondary analysis unit 130 performs alignment operations on a second batch of reads that were generated by the sequencing device 110 and not previously aligned. This process can be iteratively performed until each batch of reads is processed through the system 100. Though this example is described as having batches that are aligned and sorted, there is no requirement of the present disclosure that the batches of aligned reads also be sorted. Instead, the use of aligned and sorted reads can be employed in the system 100 or the system 300 in an effort to obtain performance enhance such as a reduced runtime, as described below.

The fusion candidate identification module 140 can obtain a batch of aligned and sorted reads that were aligned by the read alignment unit 136 and determine whether the batch of aligned and sorted reads includes one or more gene fusion candidates. In some implementations, if the received batch includes aligned and sorted reads, then the fusion candidate identification module 140 can evaluate the sorted reads of a batch where the genomic interval corresponding to the batch overlaps a breakpoint of at least one fusion candidate. This can reduce the number of fusion candidates that require downstream analysis. In other implementations, if the received batch includes aligned reads that were not sorted, then the fusion candidate identification module 140 can evaluate each of the aligned reads in the batch to determine if the aligned read is a fusion candidate. In some implementations, operation of determining, by the fusion candidate identification module 140, whether the batch of reads includes one or more fusion candidates includes determining, by the fusion candidate identification module 140, wherein the batch of reads includes one or more split-read alignments, one or more discordant read pairs, one or more soft-clipped alignments, or a combination thereof.

In some implementations, the fusion candidate identification module 140 can be configured to identify split-read alignments as fusion candidates. The fusion candidate identification module 140 can identify split-read alignments by analyzing the genes of a reference sequence to which each particular read in a batch of aligned reads was aligned. If the fusion candidate identification module 140 determines that a read maps to a single gene, then the fusion candidate identification module 140 can determine that the read is not a split-read. Alternatively, if fusion candidate identification module 140 determines that a read aligns to two different genes, then the read can be determined to be a split-read. In such implementations, the split-read can be determined to be a fusion candidate. A read can be determined to align to two different reads if, for example, a first subset of nucleotides of the read are aligned to a first parent gene of the reference genome and a second subset of nucleotides of the read are aligned to a second parent gene of the reference genome. In some implementations, the first subset of nucleotides may be a prefix of the read and the second subset of nucleotides may be a suffix of the read. If the fusion candidate identification module 140 is configured to identify split-reads, data identifying the split-reads, if any, can be stored in the memory device 120.

In some implementations, the fusion candidate identification module 140 can be configured to identify discordant read pairs as fusion candidates. The fusion candidate identification module 140 can identify discordant read pairs by analyzing the genes of a reference sequence to which each particular read pair in a batch of aligned reads was aligned. If the read pair aligns to a reference sequence, and the orientation and range of the alignment is an expected orientation and range, then the read pair is determined to not be a discordant read. Alternatively, if the read pair aligns to a reference sequence, and the orientation or range of the alignment is unexpected, then read pair is determined to be a discordant read pair. In such implementations, if one read in the pair maps to one parent gene and the other maps to another parent gene, the discordant read can be determined to be a fusion candidate. If the fusion candidate identification module 140 is configured to identify discordant reads, data identifying the discordant reads, if any, can be stored in the memory device 120.

In some implementations, the fusion candidate identification module 140 can be configured to identify soft-clipped alignments. The fusion candidate identification module 140 can identify soft-clipped alignments by analyzing the genes of a reference sequence to which each particular aligned read in a batch of aligned reads was aligned. In some implementations, the fusion candidate identification module 140 can determine if the read is aligned to a single location in the reference genome in its entirety. If the fusion candidate identification module 140 determines that the read was aligned to a single location in the reference genome in its entirety, then the fusion candidate identification module 140 can determine that the read is not a soft-clipped read. Alternatively, if the fusion candidate identification module 140 determines that only a portion of the read is aligned to the reference genome, then the fusion candidate identification module 140 can determine that the read is a soft-clipped read. If aligned portion of the read maps to one parent gene and the unaligned portion is determined to have a sequence similar to another parent gene, then the soft-clipped read is determined to be a fusion candidate. If the fusion candidate identification module 140 is configured to identify soft-clipped reads, data identifying the soft-clipped reads, if any, can be stored in the memory device 120 as a gene fusion candidate.

The fusion candidate filtering module 150 can obtain data describing a set of fusion candidates identified by the fusion candidate identification module 140. In some implementations, the fusion candidate filtering module can access the memory device 120 and obtain data describing the fusion candidates from the memory device 120. In other implementations, the fusion candidate filtering module can receive data describing fusion candidates from the output of a preceding module such as the fusion candidate identification module 140. The fusion candidate filtering module 150 can use one or more filters to filter the data describing the set of fusion candidates in order to identify a filtered set of gene fusion candidates that is less than the entire set of gene fusion candidates. In some implementations, these filters are applied in a single stage. For example, each of one or more filters can be applied and each fusion candidate in the set of fusion candidates can be evaluated against each of the one or more filters. However, in other implementations, multi-stage filtering approaches can be employed. In such implementations, a first set of one or more filters is applied to the initial set of fusion candidates identified by the fusion candidate identification module 140. Then, a second set of one or more filters is applied to the first set of filtered fusion candidates that remain after application of the first filtering stage. Additional filtering stages can also be applied as necessary to achieve an optimal filtered set of fusion candidates.

In some implementations, the fusion candidate filtering module 150 can filter the set of fusion candidates to account for duplicative fusion candidates that result from high depths of coverage used during short read sequencing. For example, a pileup that occurs from 30× sequencing may result in the fusion candidate identification module 140 identifying up to 30 fusion candidates that are duplicative. The fusion candidate filtering module 150 can remove such duplicate fusion candidates by applying a filter to characteristics of the fusion candidates to check for duplicates. For example, the fusion candidate filtering module 150 can determine whether multiple fusion candidates are aligned to the same parent gene, aligned to a portion of the reference genome spanning the same or similar breakpoint, or a combination thereof. If the fusion candidate filtering module 150 identifies multiple fusion candidates that are aligned to the same parent gene, aligned to a portion of the reference genome spanning the same or similar breakpoint, or a combination thereof, the fusion candidate filtering module 150 can determine that the fusion candidates are duplicative and select only one of the fusion candidates as a representative fusion candidate. In such instances, the remaining fusion candidates that are aligned to the same parent gene, aligned to a portion of the reference genome spanning the same or similar breakpoint, or a combination thereof, can be discarded without further downstream analysis. The representative fusion candidate can then be added to a set of filtered fusion candidates in a memory device such as memory device 120.

Alternatively, or in addition, the fusion candidate filtering module 150 can filter the set of fusion candidates based on one or more rule conditions. For example, the fusion candidate filtering module 150 can analyze each fusion candidate and determine whether the fusion candidate has one or more attributes satisfy the one or more rules conditions employed by the filtering modules 150. In some implementations, the one or more rule conditions can include a position of the alignment of each portion of a fusion candidate, a distance of overlap of the alignment with respect to a breakpoint spanned by the fusion candidate, an orientation of the alignment of the fusion candidate, a read alignment quality of the fusion candidate, an additional mapping location of the fusion candidate, or any combination thereof.

By way of example, one or more rule conditions can be used by the fusion candidate filtering module 150 to filter fusion candidates based on alignment position. In some implementations, for example, the fusion candidate filtering module 150 can be configured to use a rule condition that filters out fusion candidates having a read aligned to a reference sequence in a manner that the span of the alignment crosses a fusion breakpoint by more than a predetermined number of nucleotides. In some implementations, the predetermined number of nucleotides of this rule condition can be 8 nucleotides. Alternatively, or in addition, the fusion candidate filtering module 150 can be configured to filter out fusion candidates having a read aligned to a reference sequence in a manner that the span of the alignment on the reference sequence does not reach within a predetermined threshold number of nucleotides of the fusion breakpoint. In some implementations, the predetermined threshold number of nucleotides for this rule condition can be 50 nucleotides.

Alternatively, or in addition, the fusion candidate filtering module 150 can be configured to use a rule condition that filters out fusion candidates having a read aligned to a reference sequence in manner that the aligned portions of the read at the two fusion breakpoints share at least a predetermined number of nucleotides. In some implementations, the predetermined number of shared nucleotides can include at least 8 nucleotides.

By way of another example, one or more rule conditions can be used by the fusion candidate filtering module 150 to filter fusion candidates based on orientation. In some implementations, for example, the fusion candidate filtering module 150 can be configured to use a rule condition that filters out fusion candidates having an orientation of an alignment indicating that a nucleotide sequence of at least one of the parent genes is reversed in the fusion transcript.

By way of another example, one or more rule conditions can be used by the fusion candidate filtering module 150 to filter fusion candidates based on mapping quality. In some implementations, for example, the fusion candidate filtering module 150 can be configured to use a rule condition that filters out fusion candidates having a read alignment that has a mapping quality score that does not satisfy a predetermined threshold.

By way of another example, one or more rule conditions can be used by the fusion candidate filtering module 150 to filter fusion candidates based on additional mapping locations. In some implementations, for example, the fusion candidate filtering module 150 can be configured to use a rule condition that filters out fusion candidates based on a determination that a portion of the read of the fusion candidate maps to multiple locations of the reference sequence. In some implementations, the fusion candidate filtering module 150 can be configured to exclude locations which are annotated to be homologous genes.

The fusion candidates that satisfy each of the one or more rule conditions can be added to a set of filtered fusion candidates in a memory device such as memory device 120. The fusion candidates that do not satisfy each of the one or more rule conditions can be discarded without further downstream analysis. In some implementations, rule condition based filtering of fusion candidates can be applied as a second stage filter after application of a first stage de-duplication filter. In other implementations, the rule condition based filtering of fusion candidates can be applied as the first stage of filtering, and then de-duplication filter can be applied as a second stage filter. In other implementations, the rule condition-based filtering can be applied as a single stage filter without prior de-duplication filtering. Filtering fusion candidates based on one or more of these rule conditions can significantly reduce the number of fusion candidates that need to be further processed downstream.

Downstream processing can be performed on each fusion candidate in the filtered set of fusion candidates output by the fusion candidate filtering module 150. The downstream processing includes execution of the feature set generation module 160, machine learning model 170, gene fusion determination module 180, and output API module 190. Such downstream processing can be used to determine whether a candidate fusion candidate corresponds to a valid gene fusion.

The feature set generation module 160 can draw on data from multiple data sources to identify the set of data attributes on which to perform feature extraction. These data sources include attribute data stored in the memory 120 about the fusion candidate that includes (i) the read(s) of the fusion candidate, (ii) portion(s) of the reference sequence locations to which the reads of the fusion candidate were aligned, and (iii) annotations of the segments of the reference genome to which the particular gene fusion candidate was aligned. In some implementations, the annotations can include gene exon annotations, annotations indicating the presence of homologous genes, annotations indicating a list of enriched genes, or a combination thereof.

The data sources that the feature set generation module 160 can also include data that is generated by the read alignment unit 136 during the alignment process. In some implementations, the feature set generation module 160 can derive feature data from the data generated by the read alignment unit 136 during alignment of the fusion candidate. For example, the feature set generation module 160 can derive, from data generated by the read alignment unit 136, information, such as a variant allele frequency count, a count of unique read alignments, a read coverage across the transcript, a MAPQ score, data that indicates a homology between parent genes, or a combination thereof.

The feature set generation module 160 can be used to generate feature data that represents one or more of the aforementioned attributes of a fusion candidate drawing from multiple data source and encode the feature data into one or more data structures 162 for input to machine learning model 170. For example, in some implementations, the entire set of features extracted from attributes of the fusion candidate may be encoded into single vector 162 that incorporated into the machine learning module 170. For example, in the scenario of a split-read or soft-clipped alignments each of the features extracted from attributes of these types of fusion candidates can be encoded into a single vectors 162.

In other implementations, the feature data may be that is extracted from attributes of fusion candidates may be encoded input multiple vectors. In such a scenario, the input vector 162 may be comprised of a pair of input vectors 162*a*, 162*b*. For example, in the scenario of a split-read fusion candidate, each of the features extracted from attributes related to the prefix of the split-read including features representing the nucleotides of the prefix of the split-read, the features representing the segment of the reference sequence to which the prefix aligns, and any other features extracted from the aforementioned attributes relating to the prefix, or any combination thereof may be encoded into the input vector 162*a*. Likewise, in such an implementation, each of the features extracted from attributes related to the suffix of the split-read including the features representing nucleotides of the suffix of the split-read, the features representing the segment of the reference sequence to which the suffix aligns, and any other features extracted from the aforementioned attributes relating to the suffix, or any combination thereof may be encoded into the input vector 162*b*. By way of another example, when a discordant read pair is identified as a fusion candidate, then extracted features representing the first read of the discordant read pair, extracted features representing the portion of the reference sequence it was aligned to, features extracted from attributes related to the first read of the discordant read pair, or any combination thereof, may be encoded into the input vector 162*a*. Likewise, in such an example, the extracted features representing the second read of the discordant read pair, extracted features representing the portion of the reference sequence it was aligned to, features extracted from attributes related to the second read of the discordant read pair, or any combination thereof, may be encoded into the input vector 162*b*.

Each of the one or more vectors 162 can numerically represent the generated feature data, with the feature data including any of the features extracted from the fusion candidate or any of the features extracted from data received from the read alignment unit 136 related to the fusion candidate and stored in memory 120. For example, each vector 162 or 162a, 162b can include a plurality of fields that each correspond to a particular feature of a particular read of a particular fusion candidate. Dependent on the particular fusion candidate, this can result in one or more input vectors, as described above. The feature set generation module 160 can determine a numerical value for each of the fields that describes the extent that the particular feature was expressed in the attributes of the particular read of the fusion candidate. The determined numerical values for each of the fields can be used to encode the generated feature data representing attributes of the reads of the fusion candidate into the one or more respective vectors 162. The generated one or more vectors 162a, 162b, which numerically represent the corresponding reads of the fusion candidate, are provided as inputs to the machine learning model 170. In some implementations, even if multiple conceptual vectors are generated for a fusion candidate, the multiple conceptual vectors can be contacted into a single vector 162 that can be input into the machine learning model 170. In such an implementations, if multiple vectors were warranted in (i) certain split-read implementations where features of the prefix are assigned to a first vector and features of the suffix are assigned to the second vector or (ii) in discordant pair implementations, a first portion of the single vector can correspond to the conceptual first vector and second portion of the single vector could correspond to the conceptual second vector.

The machine learning model 170 can include a deep neural network that has been trained to generate a likelihood that a fusion candidate corresponds to a valid gene fusion based on the processing of input one or more input vectors 162 that represent features of a fusion candidate. A valid gene fusion is a chimeric transcript that contains a sequence from multiple genes due to rearrangement in the genome connecting a prefix of one parent gene with the suffix of another parent gene. In the context of the present disclosure, a valid gene fusion will be determined to have been predicted by the model 170 if, for example, the output data 178 generated by the machine learning model satisfies a predetermined threshold. The machine learning model 170 can include an input layer 172 for receiving input data, one or more hidden layers 174a, 174b, 174c for processing the input data received via the input layer 172, and an output layer 176 for providing output data 178. Each hidden layer 174a, 174b, 174c includes one or more weights or other parameters. The weights or other parameters of each respective hidden layer 174a, 174b, 174c can be adjusted, during training, so that the trained deep neural network produces the desired target output 178 indicating a likelihood that the one or more input vectors 162 represent a valid gene fusion based on the machine learning model 170 processing the one or more input vectors 162.

The machine learning model 170 can be trained in a number of different ways. In one implementation, the machine learning model 170 can be trained to distinguish between (i) one or more input vectors representing features extracted from attributes of valid fusion candidates and (ii) one or more input vectors representing features extracted from attributes of invalid fusion candidates. In some implementations, such training can be achieved using labeled pairs of training vectors. Each training vector can represent a training fusion candidate and be comprised of the same types of feature data as are the one or more input vectors 162 above. In such implementations, one or more input vectors 162 representing features extracted from attributes of fusion candidates can be labeled as being a valid gene fusion or an invalid gene fusion. In some implementations, the valid gene fusion label or the invalid gene fusion label can be represented as a numerical value. For example, in some implementations, a valid gene fusion label can be a "1" and an invalid gene fusion label can be a "0." In other implementations, for example, the valid gene fusion label can be a number between "0" and "1" that satisfies a predetermined threshold and an invalid gene fusion label can be a number between "0" and 1" that does not satisfy a predetermined threshold. In such implementations, the magnitude with which the number satisfies or does not satisfy the predetermined threshold is an indication of a level of confidence that the training pair of input vectors represents a valid gene fusion or an invalid gene fusion. In some implementations, satisfying a predetermined threshold can include exceeding the predetermined threshold. However, implementations can also be configured such that satisfying a threshold means not exceeding the predetermined threshold. Such implementations can include, for example, implementations where the comparator and parameters were both negated.

During training, each labeled set of one or more training vectors is provided as an input to the machine learning model 170, be processed by the machine learning model 170, and then training output generated by the machine learning model 170 is used to determine a predicted label for each labeled set of one or more training vectors. The predicted label generated by the machine learning model 170 based on the machine learning model's processing of the labeled one or more training vectors corresponding to a pair of reads for a training fusion candidate can be compared to a training label for the one or more training vectors corresponding to the one or more reads (or read portions) for the training fusion candidate. Then, the parameters of the machine learning model 170 can be adjusted based on differences between the predicted labels and the training labels. This process can iteratively continue for each of a plurality of labeled training vector(s) corresponding to a respective training fusion candidate until predicted fusion candidate labels produced by the machine learning model 170 based on processing of a set of one or more training vectors corresponding to a training fusion candidate match, within a predetermined level of error, training labels of the set of one or more training vectors corresponding to the respective training fusion candidate.

In some implementations, the labeled training fusion candidates can be obtained from a library of training fusion candidates that have been reviewed and labeled by one or more human users. However, in other implementations, the labeled training fusion candidates can include training fusion candidate that that have been generated and labeled by a simulator. In such implementations, the simulator can be used to create distributions of different categories of training fusion candidates that can be used to train the machine learning model 170. In general, if the runtime machine learning model 170 is to accept a single input vector 162, with each of the extracted feature for a fusion candidate being encoded the single input vector 162, then the machine learning model 170 is to be trained using a single input vector of the same features as input vector 162 using the training process above. Likewise, if the runtime machine learning module 170 is to accept two training vectors 162a, 162b, as described above, then the machine learning model 170 is to be trained using two input vectors that each have the same corresponding features of input vectors 162a, 162b above. That is, the type of input vectors that are to be processed at runtime are the same time of vectors that are to be used to train the model 170, using the training process described above.

During processing of input data 162 that corresponds to features extracted from attributes of a fusion candidate, the output of each hidden layer 174a, 174b, 174c can include an activation vector. The activation vector output by each respective hidden layer can be propagated through subsequent layers of the deep neural network and used by the output layer to produce output data 178. In the example of FIG. 1, the machine learning model 170 is trained to produce output data 178 that represents a combined score generated by the machine learning model 170 based on the machine learning model processing of the separate input vectors 162a, 162b that each correspond to one of the reads of the fusion candidate. This combined score 178 is ultimately produced by the output layer 176 of the trained machine learning model based on computations performed by the output layer 176 of the trained machine learning model 170 on a received activation vector from the final hidden layer 174c.

The output data 178 generated by the trained machine learning model 170 can be evaluated by a gene fusion determination module 180 to determine whether it indicates that the fusion candidate corresponding to the one or more input vectors 162 is a valid fusion candidate. In some implementations, the output data 178 can be provided to the gene fusion determination module 180 by the trained machine learning model 170. In other implementations, the system 100 can store the output 178 of the trained machine learning model 170 to a memory device such as memory device 120 for subsequent accessing by the gene fusion determination module 180.

The gene fusion determination module 180 can obtain the output data 178 generated by the machine learning model 170 and evaluate the output data 178 to determine, based on the output data 178, whether the fusion candidate corresponding to the pair 162 of input vectors 162a, 162b is valid gene fusion. In some implementations, the gene fusion determination module 180 can determine whether the fusion candidate corresponding to the one or more input vectors 162 is a valid gene fusion by comparing the output data 178 generated by the machine learning model to a predetermined threshold. If the gene fusion determination module 180 determines that the output data 178 satisfies the predetermined threshold, then the gene fusion determination module 180 can determine that the fusion candidate corresponding to the one or more input vectors 162 is a valid gene fusion. Alternatively, if the gene fusion determination module 180 determines that the output data 178 does not satisfy the predetermined threshold, then the gene fusion determination module 180 can determine that the fusion candidate corresponding to the one or more input vectors 162 is not a valid gene fusion.

In some implementations, the gene fusion determination module 180 can generate output data 182 that indicates results of the determination made by the gene fusion determination module 180 based on the gene fusion determination module's 180 evaluation of the output data 178 produced by the machine learning model 170. This output data 182 can include data identifying the gene fusion candidate that corresponds to the one or more input vectors 162 and data identifying the determination of the gene fusion determination module 180. Data identifying the determination of the gene fusion determination module 180 can include data indicating whether the gene fusion candidate that corresponds to the one or more input vectors 162 is a valid gene fusion or an invalid gene fusion. In some implementations, the output data 182 may only indicate list of valid gene fusions identified based on the output data 178, a list of invalid gene fusions identified based on the output data 178, data indicating that no valid gene fusions were identified, or any combination thereof. In some implementations, this output data 182 can be stored in the memory 182 for subsequent use by another computing module, for subsequent output to a user device, or the like.

Alternatively, or in addition, the gene fusion determination module 180 can generate output data 184 that can be provided as an input to the output application programming interface (API) module 190. The output data 184 can instruct the output API to cause an output display to output indicating whether the gene fusion candidate that corresponds to the one or more input vectors 162 is a valid gene fusion or an invalid gen fusion. In some implementations, the instructions can cause the output API module 190 to access the output data 182 stored in the memory device 120 and generate rendering data that, when rendered by a computing device coupled to the output display 195 causes the output display 195 to display (i) data identifying the fusion candidate that corresponds to the one or more input vectors 162 and (ii) data indicating whether identified fusion candidate is a valid gene fusion or an invalid gene fusion. This can include causing the output display 195 to display any of the output data 182 stored in the memory 184. In some implementations, this output can be displayed in the form of a report.

In some implementations, the gene fusion determination module 180 stores output data 182 for each gene fusion candidate in the memory device 120 based on the performance of downstream processing being performed on each fusion candidate of the filtered set of gene fusion candidates. In such implementations, the gene fusion determination module 180 may only instruct the output API module 190 to output the results of the gene fusion analysis stored in the memory 120 for each fusion candidate of the filtered set of gene fusion candidates once downstream processing of each fusion candidate is complete. In such a scenario, the output 192 provided for display on the output display 195 would include a list of valid gene fusion, a list of invalid gene fusions, or both. In other implementations, the gene fusion determination module 180 can cause the output API module 190 to output result data indicating a list of identified gene fusions, if any, upon completion of downstream processing for that particular fusion candidate.

Other types of output 192 can be provided by the output API module 190. For example, in some implementations, the output 192 can be data that causes another device such as a printer to output a report that includes (i) data identifying the fusion candidate that corresponds to the one or more vectors 162 and (ii) data indicating whether identified fusion candidate is a valid gene. In other implementations, this output data 192 can cause a speaker to output audio data that includes (i) data identifying the fusion candidate that corresponds to the one or more vectors 162 and (ii) data indicating whether identified fusion candidate is a valid gene. Other types of output data can also be triggered by the output APIR modules 190.

In some implementations, the output display 195 can be a display panel of the sequencing device 110. In other implementations, the output display 195 can be a display panel of a user device that is connected to the sequencing device 110 using one or more networks. Indeed, the sequencing device 110 can be used to communicate the output data 192 to any device having any display.

Figure 2:
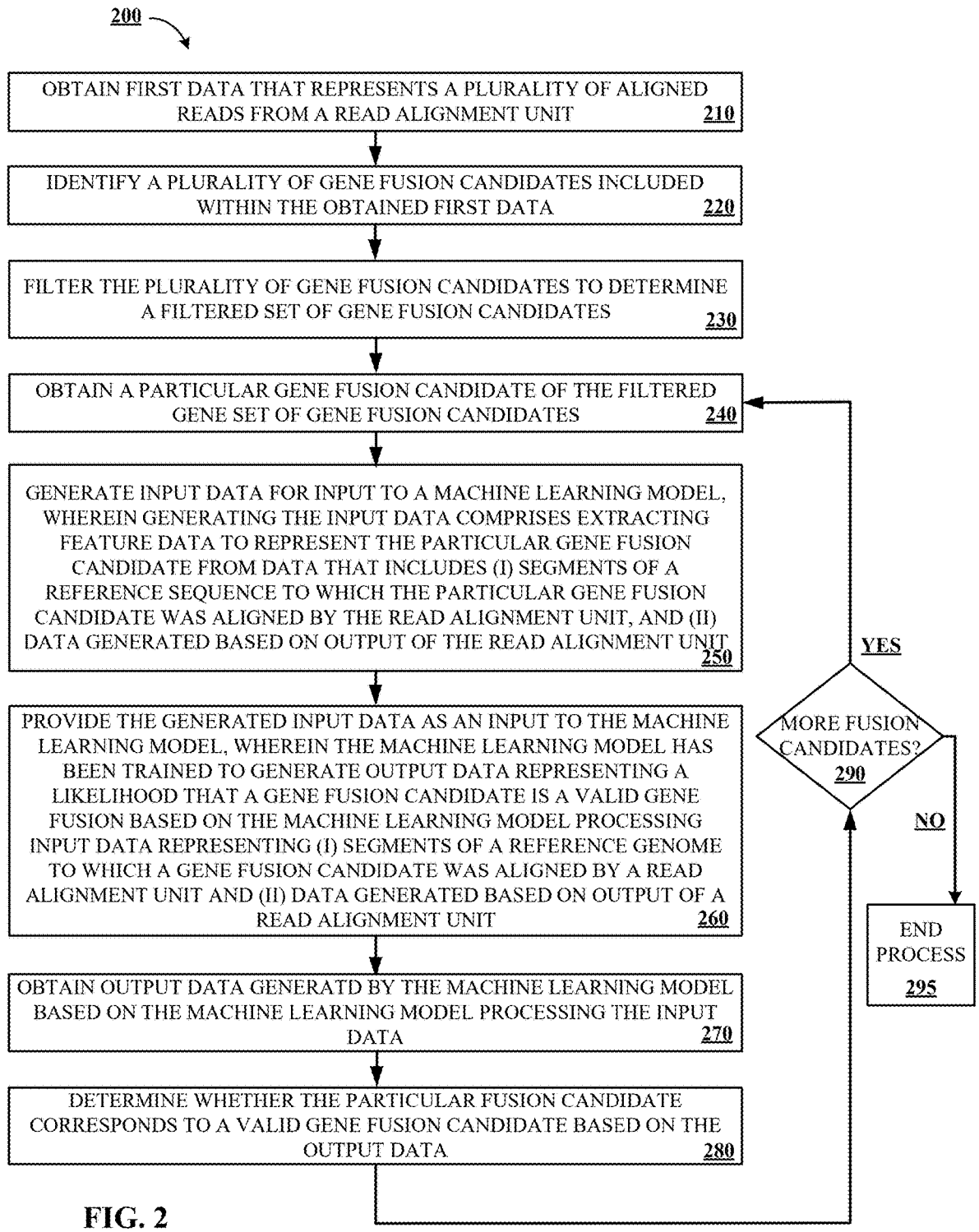
FIG. 2 is a flowchart of an example of a process for performing rapid detection of valid gene fusions.

FIG. 2 is a flowchart of an example of a process 200 for performing rapid detection of valid gene fusions. A system, such as the system 100, can begin execution of the process 200 by using one or more computers to obtain first data that represents a plurality of aligned reads from a read alignment unit (210). The system can identify a plurality of gene fusion candidates included within the obtained first data (220). The system can filter the plurality of gene fusion candidates to determine a filtered set of gene fusion candidates (230).

The system can obtain a particular gene fusion candidate of the filtered set of gene fusion candidates (240). The system can generate input data for input to a machine learning model, wherein generating the input data includes extracting feature data to represent the particular gene fusion candidate from data that includes (i) one or more segments of a reference sequence to which the particular gene fusion candidate was aligned to by the read alignment unit, and (ii) data generated based on output of the read alignment unit (250).

The system can provide the generated input data as an input to the machine learning model, wherein the machine learning model has been trained to generate output data representing a likelihood that a gene fusion candidate is a valid gene fusion based on the machine learning model processing input data representing (i) segments of a reference genome to which the particular gene fusion candidate was aligned by the read alignment unit, and (ii) data generated based on output of the read alignment unit (260). The system can obtain output data generated by the machine learning model based on the machine learning model processing the input data (270). The system can determine whether the particular fusion candidate corresponds to a valid gene fusion candidate based on the output data (280).

Upon completion of stage 280, the system can determine whether another fusion candidate of the filtered set of fusion candidates is to be evaluated (290). If the system determines that there is another fusion candidate of the filtered set of fusion candidates that is to be evaluated, then the system can continue execution of the process 200 at stage 240. Alternatively, if the system determines there is not another fusion candidate of the filtered set of fusion candidates that is to be evaluated, then the system can terminate execution of the process at stage 295. Another fusion candidate can exist in the filtered set of fusion candidates if the set of set of fusion candidates has not been exhausted.

Figure 3:
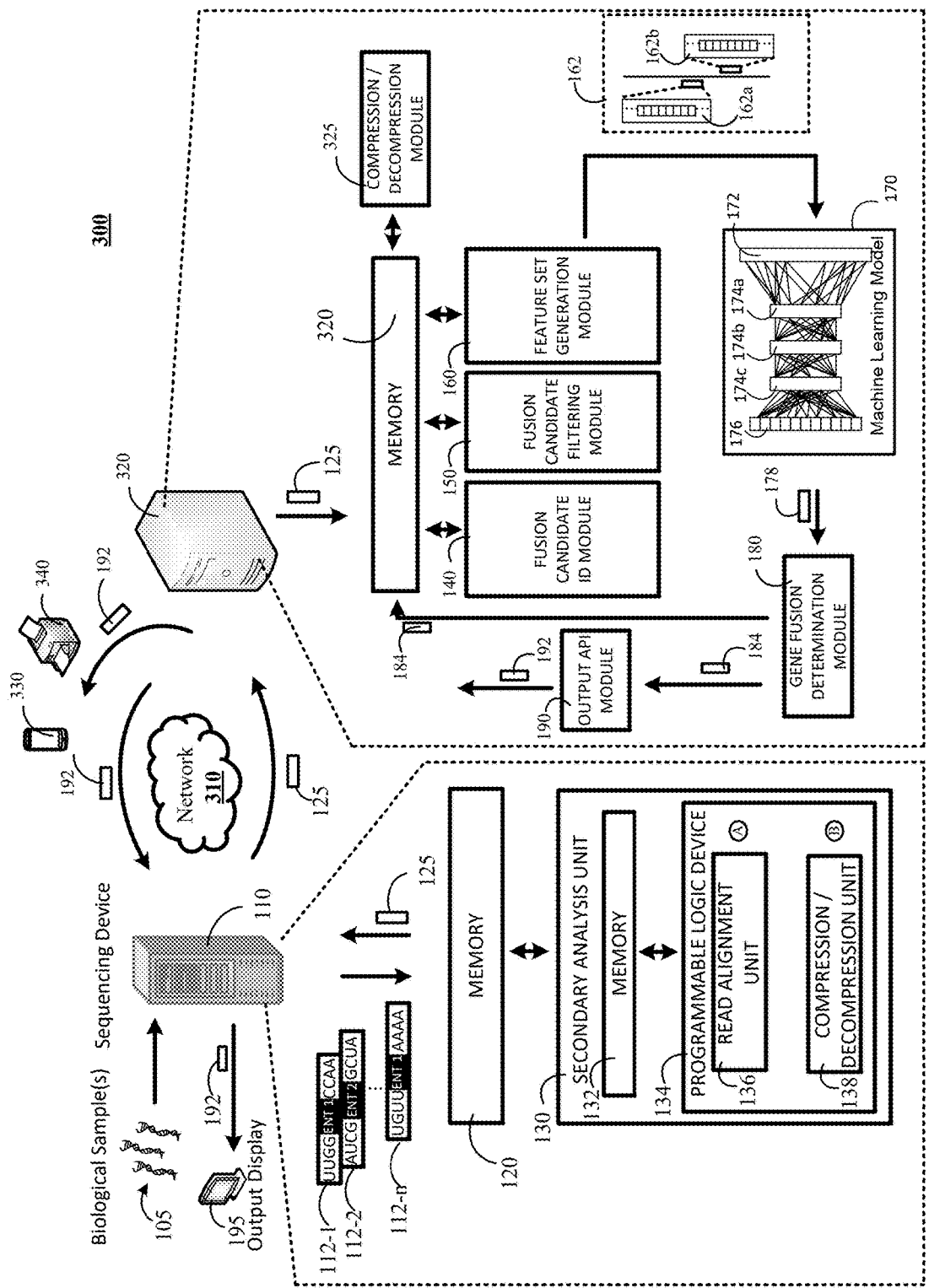
FIG. 3 is a block diagram of another example of a system for rapid detection of valid gene fusions.

FIG. 3 is a block diagram of another example of a system 300 for rapid detection of valid gene fusions. The system 300 performs the same functions as the system 100 in that the system 300 uses a sequencing device 110 to generate RNA (or DNA) sequence reads 112, uses a secondary analysis unit 130 to align the RNA sequence reads 112 to a reference sequence, uses a fusion candidate identification module 140 to identify fusion candidates, uses a fusion candidate filtering module 150 to determine a filtered set of fusion candidates for downstream analysis, and then performs downstream analysis of the filtered set of fusion candidates to identify valid gene fusions using a feature set generation module 160, a machine learning model 170, a gene fusion determination module 190, and an output API module 190. Each of these functional units, modules, or model perform the same functions as was attributed to them in the description of system 100 of FIG. 1.

The difference between system 300 and system 100 is that the fusion candidate identification, fusion candidate filtering, and downstream analysis of the filtered set of fusion candidates is performed on a different computer 320 and not within the sequencing device 110. Accordingly, differences between system 300 and system 100 lie in how the aligned reads are packed and communicated to the computer 320 for gene fusion analysis using the network 310, unpackaged by the computer 320, and how the gene fusion results are packaged and transmitted to another device with a corresponding display for output.

In more detail, the sequencing device 110 can sequence the biological sample 105 and generate RNA reads 112-1, 112-2, 112-*n*, where "n" is any positive integer greater than 0 as described with reference to the system 100. Though RNA reads are being used as an example, the system can also perform the same processes on DNA reads. The sequencing device 110 can store the reads 112-1, 112-2, 112-*n* in the memory 120. In some implementations, the reads 112-1, 112-2, 112-*n* may be in a compressed format.

The secondary analysis unit 130 can obtain the reads 112-1, 112-2, 112-*n* and store the reads 112-1, 112-2, 122-*n* in the memory 132 of the secondary analysis unit 130. In some implementations, this can include a control program of the sequencing device 110 streaming the reads 112-1, 112-2, 112-*n* into the memory 132 of the secondary analysis unit 130. In other implementations, the secondary analysis unit 130 can request the reads 112-1, 112-2, 122-*n*. If the reads 112-1, 112-2, 112-*n* are compressed, the programmable logic device 134 of the secondary analysis unit 130 can be configured into state B as a decompression unit 138 and be used to decompress the reads 112-1, 112-2, 112-*n*. The programmable logic device 134 can then be reconfigured into state A as a read alignment unit and used to align the reads 112-1, 112-2, 112-*n* to a reference sequence.

The secondary analysis unit 130 can be reconfigured back into state B as a compression unit and use the compression unit to compress the aligned reads to prepare the aligned reads for transmission to the computer 320. In this example, compressing of the first batch of aligned reads includes compressing not only the aligned reads, but also the data generated by the read alignment unit 136 related to the aligned reads that will be used for gene fusion analysis. This data is described with reference to the system 100 of FIG. 1 and can include, for example, a variant allele frequency count, a count of unique read alignments, a read coverage across the transcript, a MAPQ score, data that indicates a homology between parent genes, or a combination thereof. In addition, other data that may be compressed into the first batch of aligned reads can include (i) the reads of the fusion candidate, (ii) portion of the reference sequence locations to which the reads of the fusion candidate were aligned, and (iii) annotations of the segments of the reference genome to which the particular gene fusion candidate was aligned. In some implementations, the annotations can include gene exon annotations, annotations indicating the presence of homologous genes, annotations indicating a list of enriched genes, or a combination thereof.

After compressing the aligned reads, the secondary analysis unit 130 can store the first batch of compressed reads in the memory 120. Then, the sequencing device 110 can transmit the first batch 125 of aligned reads to the computer 320 across the network 310 for gene fusion analysis. The network 310 can include one or more wired networks, one or more wireless networks, or a combination thereof. In different implementations, the network 310 may be one or more of a wired Ethernet, a wired optical network, a LAN, a WAN, a cellular network, the Internet, or a combination thereof. In some implementations, the computer 320 can be a remote cloud server. However, in other implementations, the computer 320 can connected to the sequencing device 110 via a direct connection such as a direct Ethernet connection, a USB-C connection, or the like. Though the first batch of reads is compressed prior to communication in this example of FIG. 300, there is no requirement that compression be used. Instead, compressing is provided as a method to reduce the consumption of network bandwidth and minimize storage costs, which can provide significant technological benefits and reduced costs when dealing with large data sizes of genomes.

In some implementations, the first batch of aligned reads includes an entire set of reads generated for the sample 105. In other implementations, the first batch of aligned reads is only a portion of the entire set of reads generated for the sample 105 and a batch processing system can be used to facilitate parallel processing. For example, in some implementations, after the secondary analysis unit stores the first batch of aligned reads in the memory 120, the secondary analysis unit 130 obtains a second batch of reads that are not yet aligned for storage in the memory 132. Then, the secondary analysis unit 130 can perform decompression, if the second batch of reads was compressed, and alignment of the second batch of reads while the computer 320 is performing gene fusion analysis of the first batch of reads. Such parallel processing facilitated via batch processing of the reads can significantly reduce the runtime of the system 300 that is required to determine valid gene fusions for reads of a sample 105.

The computer 320 can receive the first batch of reads 125 via the network 310 and store the first batch of reads in the memory 320. If the first batch of reads 125 is compressed, the computer 320 can use the compression/decompression module 325 to decompress the first batch of reads and store the first batch of reads in the memory 320. The computer 320 can then execute the gene fusion analysis pipeline of the fusion candidate identification module 140, the fusion candidate filtering module 150, the feature set generation module 160, the machine learning model 170, the gene fusion determination module 180, and the output API module 190 in the same manner as described with reference to system 100 of FIG. 1.

The output 192 can be provided to a number of different devices via the network 310. By way of example, the output data can be transmitted to the sequencing device for output on a display 195 of the sequencer. Alternatively, or in addition, the output 192 can be provided for display on a display of a user device 330 via the network 310. The user device 330 can include a smartphone, tablet computer, laptop computer, desktop computer, or any other computer with a display. Alternatively, or in addition, the output 192 can also be provided for output via a printer 340 via the network 310. In such implementations, the output may be a hardcopy report of the determined valid gene fusions.

Figure 4:
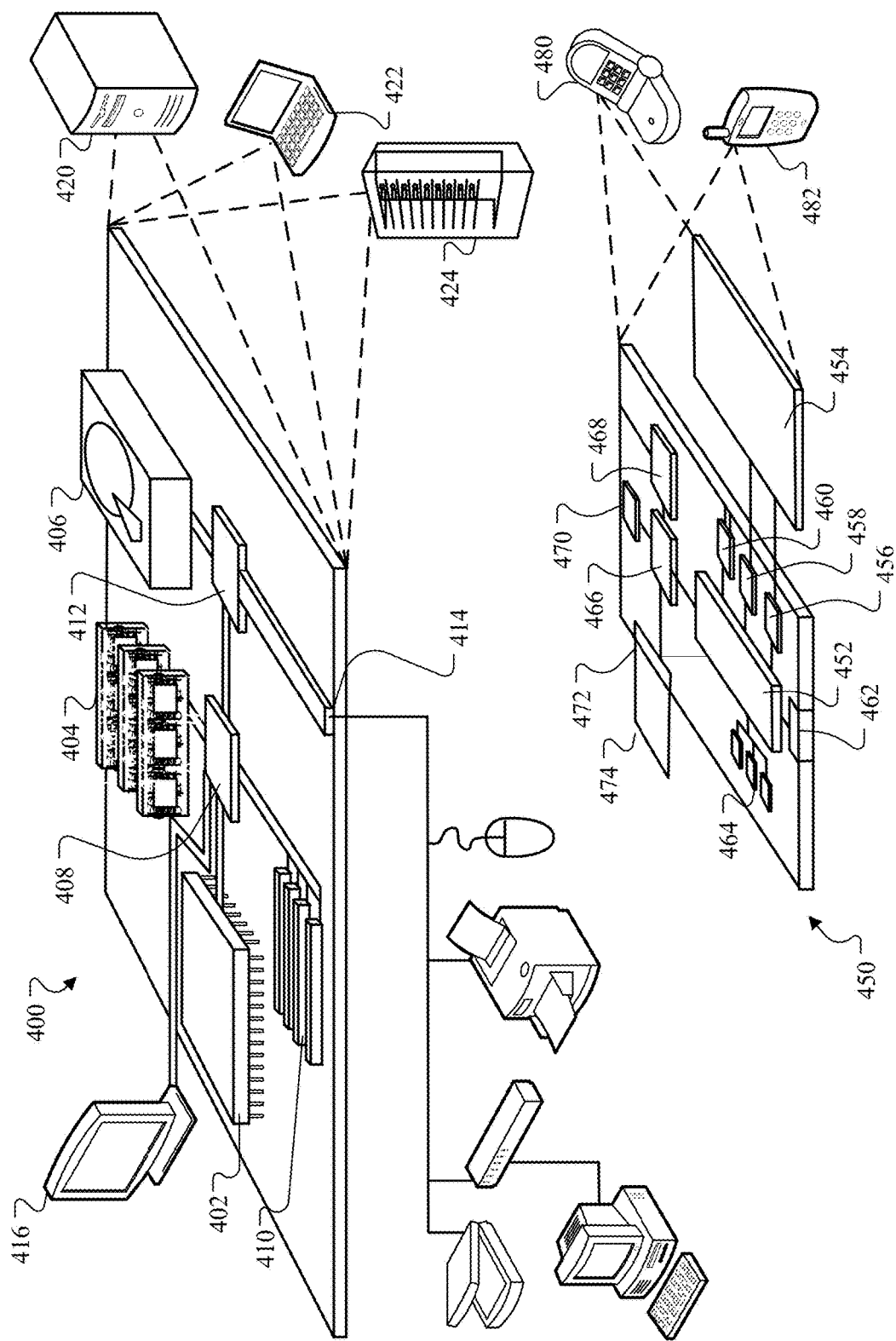
FIG. 4 is a block diagram of system components that can be used to implement a system for rapid detection of valid gene fusions.

FIG. 4 is a block diagram of system components that can be used to implement a system for rapid detection of gene fusions.

Computing device 400 is intended to represent various forms of digital computers, such as laptops, desktops, workstations, personal digital assistants, servers, blade servers, mainframes, and other appropriate computers. Computing device 450 is intended to represent various forms of mobile devices, such as personal digital assistants, cellular telephones, smartphones, and other similar computing devices. Additionally, computing device 400 or 450 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 400 includes a processor 402, memory 404, a storage device 406, a high-speed interface 408 connecting to memory 404 and high-speed expansion ports 410, and a low speed interface 412 connecting to low speed bus 414 and storage device 408. Each of the components 402, 404, 406, 408, 410, and 412, are interconnected using various busses, and can be mounted on a common motherboard or in other manners as appropriate. The processor 402 can process instructions for execution within the computing device 400, including instructions stored in the memory 404 or on the storage device 408 to display graphical information for a GUI on an external input/output device, such as display 416 coupled to high speed interface 408. In other implementations, multiple processors and/or multiple buses can be used, as appropriate, along with multiple memories and types of memory. Also, multiple computing devices 400 can be connected, with each device providing portions of the necessary operations, e.g., as a server bank, a group of blade servers, or a multi-processor system.

The memory 404 stores information within the computing device 400. In one implementation, the memory 404 is a volatile memory unit or units. In another implementation, the memory 404 is a non-volatile memory unit or units. The memory 404 can also be another form of computer-readable medium, such as a magnetic or optical disk.

The storage device 408 is capable of providing mass storage for the computing device 400. In one implementation, the storage device 408 can be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 404, the storage device 408, or memory on processor 402.

The high-speed controller 408 manages bandwidth-intensive operations for the computing device 400, while the low speed controller 412 manages lower bandwidth intensive operations. Such allocation of functions is only an example. In one implementation, the high-speed controller 408 is coupled to memory 404, display 416, e.g., through a graphics processor or accelerator, and to high-speed expansion ports 410, which can accept various expansion cards (not shown). In the implementation, low-speed controller 412 is coupled to storage device 408 and low-speed expansion port 414. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 400 can be implemented in a number of different forms, as shown in the figure. For example, it can be implemented as a standard server 420, or multiple times in a group of such servers. It can also be implemented as part of a rack server system 424. In addition, it can be implemented in a personal computer such as a laptop computer 422. Alternatively, components from computing device 400 can be combined with other components in a mobile device (not shown), such as device 450. Each of such devices can contain one or more of computing device 400, 450, and an entire system can be made up of multiple computing devices 400, 450 communicating with each other.

The computing device 400 can be implemented in a number of different forms, as shown in the figure. For example, it can be implemented as a standard server 420, or multiple times in a group of such servers. It can also be implemented as part of a rack server system 424. In addition, it can be implemented in a personal computer such as a laptop computer 422. Alternatively, components from computing device 400 can be combined with other components in a mobile device (not shown), such as device 450. Each of such devices can contain one or more of computing device 400, 450, and an entire system can be made up of multiple computing devices 400, 450 communicating with each other.

Computing device 450 includes a processor 452, memory 464, and an input/output device such as a display 454, a communication interface 466, and a transceiver 468, among other components. The device 450 can also be provided with a storage device, such as a micro-drive or other device, to provide additional storage. Each of the components 450, 452, 464, 454, 466, and 468, are interconnected using various buses, and several of the components can be mounted on a common motherboard or in other manners as appropriate.

The processor 452 can execute instructions within the computing device 450, including instructions stored in the memory 464. The processor can be implemented as a chipset of chips that include separate and multiple analog and digital processors. Additionally, the processor can be implemented using any of a number of architectures. For example, the processor 410 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 450, such as control of user interfaces, applications run by device 450, and wireless communication by device 450.

Processor 452 can communicate with a user through control interface 458 and display interface 456 coupled to a display 454. The display 454 can be, for example, a TFT (Thin-Film-Transistor Liquid Crystal Display) display or an OLED (Organic Light Emitting Diode) display, or other appropriate display technology. The display interface 456 can comprise appropriate circuitry for driving the display 454 to present graphical and other information to a user. The control interface 458 can receive commands from a user and convert them for submission to the processor 452. In addition, an external interface 462 can be provided in communication with processor 452, so as to enable near area communication of device 450 with other devices. External interface 462 can provide, for example, for wired communication in some implementations, or for wireless communication in other implementations, and multiple interfaces can also be used.

The memory 464 stores information within the computing device 450. The memory 464 can be implemented as one or more of a computer-readable medium or media, a volatile memory unit or units, or a non-volatile memory unit or units. Expansion memory 474 can also be provided and connected to device 450 through expansion interface 472, which can include, for example, a SIMM (Single In Line Memory Module) card interface. Such expansion memory 474 can provide extra storage space for device 450, or can also store applications or other information for device 450. Specifically, expansion memory 474 can include instructions to carry out or supplement the processes described above, and can also include secure information. Thus, for example, expansion memory 474 can be provided as a security module for device 450, and can be programmed with instructions that permit secure use of device 450. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 474, or memory on processor 452 that can be received, for example, over transceiver 468 or external interface 462.

Device 450 can communicate wirelessly through communication interface 466, which can include digital signal processing circuitry where necessary. Communication interface 466 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 468. In addition, short-range communication can occur, such as using a Bluetooth, Wi-Fi, or other such transceiver (not shown). In addition, GPS (Global Positioning System) receiver module 470 can provide additional navigation- and location-related wireless data to device 450, which can be used as appropriate by applications running on device 450.

Device 450 can also communicate audibly using audio codec 460, which can receive spoken information from a user and convert it to usable digital information. Audio codec 460 can likewise generate audible sound for a user, such as through a speaker, e.g., in a handset of device 450. Such sound can include sound from voice telephone calls, can include recorded sound, e.g., voice messages, music files, etc. and can also include sound generated by applications operating on device 450.

The computing device 450 can be implemented in a number of different forms, as shown in the figure. For example, it can be implemented as a cellular telephone 480. It can also be implemented as part of a smartphone 482, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Other Embodiments

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A computer-implemented method for identifying one or more gene fusions in a biological sample, the method comprising:
for each of millions of reference sequence locations:
obtaining, by one or more computers, first data corresponding to a pileup of aligned reads produced using short read sequencing and having a high depth of coverage at the reference sequence location from a read alignment unit;
determining, by one or more computers, whether one or more gene fusion candidates are included within the obtained first data;
based on a determination that one or more gene fusion candidates are included within the obtained first data,
(i) removing, by one or more computers, duplicate fusion candidate occurrences resulting from the high depth of coverage at the reference sequence location, and (ii) adding the remaining gene fusion candidates to a filtered set of gene fusion candidates;
for each particular gene fusion candidate of the filtered set of gene fusion candidates:
generating, by one or more computers, input data for input to a machine learning model, wherein generating the input data comprises extracting feature data to represent the particular gene fusion candidate from data that includes:
(i) one or more segments of a reference sequence to which the particular gene fusion candidate was aligned by the read alignment unit, and
(ii) data generated based on output of the read alignment unit, wherein the data generated based on the output of the read alignment unit includes one or more of a variant allele frequency count, a count of unique read alignments, or a MAPQ score;
providing, by one or more computers, the generated input data as an input to the machine learning model, wherein the machine learning model has been trained using labeled training vectors, each labeled training vector representing a training fusion candidate and comprising (i) one or more segments of a reference sequence to which the training fusion candidate was aligned, and (ii) one or more of a variant allele frequency count, a count of unique read alignments, or a MAPQ score to generate output data representing a likelihood that a gene fusion candidate is a valid gene fusion based on the machine learning model processing input data representing (i) one or more segments of a reference sequence to which the particular gene fusion candidate was aligned to by the read alignment unit, and (ii) data generated based on output of the read alignment unit, wherein the data generated based on the output of the read alignment unit includes one or more of a variant allele frequency count, a count of unique read alignments, or a MAPQ score;
obtaining, by one or more computers, output data generated by the machine learning model based on the machine learning model processing the generated input data; and
determining, by one or more computers, whether the particular fusion candidate corresponds to a valid gene fusion candidate based on the output data.

2. The method of claim 1,
wherein generating the input data further comprises extracting feature data that includes annotation data describing annotations of the segments of the reference sequence to which the particular gene fusion candidate was aligned to by the read alignment unit; and
wherein the machine learning model has been trained to generate output data representing a likelihood that a gene fusion candidate is a valid gene fusion candidate based on the machine learning model processing input data representing:
(i) one or more segments of a reference sequence to which the particular gene fusion candidate was aligned to by the read alignment unit,
(ii) annotation data describing annotations of the segments of the reference sequence to which the particular gene fusion candidate was aligned to by the read alignment unit, and
(iii) data generated based on output of the read alignment unit.

3. The method of claim 1, wherein determining, by one or more computers, whether one or more gene fusion candidates are included within the obtained first data comprises identifying, by one or more computers, a plurality of split-read alignments.

4. The method of claim 1, wherein determining, by one or more computers, whether one or more gene fusion candidates are included within the obtained first data comprises identifying, by one or more computers, a plurality of discordant read pair alignments.

5. The method of claim 1, wherein the read alignment unit is implemented using a set of one or more processing engines that are configured using hardware logic circuits that have been physically arranged to perform operations, using the hardware logic circuits, to:
(i) receive data representing a first read,
(ii) map the data representing the first read to one or more portions of a reference sequence to identify one or more matching reference sequence locations,
(iii) generate one or more alignment scores corresponding to each of the matching reference sequence locations for the first read,
(iv) select one or more candidate alignments for the first read based on the one or more alignment scores, and
(v) output data representing a candidate alignment for the first read.

6. The method of claim 1, wherein the read alignment unit is implemented using a set of one or more processing engines by using one or more central processing units (CPUs) or one or more graphics processing units (GPUs) to execute software instructions that cause the one or more CPUs or one or more GPUS to:
(i) receive data representing a first read,
(ii) map the data representing the first read to one or more portions of a reference sequence to identify one or more matching reference sequence locations for the first read,
(iii) generate one or more alignment scores corresponding to each of the matching reference sequence locations for the first read,
(iv) select one or more candidate alignments for the first read based on the one or more alignment scores, and
(v) output data representing a candidate alignment for the first read.

7. The method of claim 1, the method further comprising:
wherein obtaining, by one or more computers, first data that represents the pileup of aligned reads from a read alignment unit comprises obtaining, by one or more computers, the pileup of aligned reads from a memory device and performing one or more of the operations of claim 1 while the read alignment unit aligns a second pileup of reads that are not yet aligned.

8. The method of claim 1, wherein determining whether the particular fusion candidate corresponds to a valid gene fusion candidate based on the output data comprises:
determining, by one or more computers, whether the output data satisfies a predetermined threshold; and
based on determining that the output data satisfies the predetermined thresholds, determining that the particular fusion candidate corresponds to a valid gene fusion candidate.

9. The method of claim 1, wherein determining whether the particular fusion candidate corresponds to a valid gene fusion candidate based on the output data comprises:
determining, by one or more computers, whether the output data satisfies a predetermined threshold; and
based on determining that the output data does not satisfy the predetermined thresholds, determining that the particular fusion candidate does not correspond to a valid gene fusion candidate.

10. The method of claim 1, wherein the high depth of coverage at the reference sequence location is 30× coverage.

11. The method of claim 1, wherein the data generated based on the output of the read alignment unit includes data that indicates a homology between parent genes.

12. The method of claim 11, wherein providing, by one or more computers, the generated input data as an input to the machine learning model further comprises:
providing, by one or more computers, the generated input data as an input to the machine learning model, wherein the machine learning model has been trained using labeled training vectors, each labeled training vector representing a training fusion candidate and comprising (i) one or more segments of a reference sequence to which the training fusion candidate was aligned, and (ii) one or more of a variant allele frequency count, a count of unique read alignments, a MAPQ score, and data that indicates a homology between parent genes to generate output data representing a likelihood that a gene fusion candidate is a valid gene fusion based on the machine learning model processing input data representing (i) one or more segments of a reference sequence to which the particular gene fusion candidate was aligned to by the read alignment unit, and (ii) data generated based on output of the read alignment unit, wherein the data generated based on the output of the read alignment unit includes one or more of a variant allele frequency count, a count of unique read alignments, a MAPQ score, and data that indicates a homology between parent genes.

13. The method of claim 1, the method further comprising:
based on a determination that one or more gene fusion candidates are not included within the obtained first data, determining to not add any gene fusion candidates to the filtered set of gene fusion candidates.

14. A system for identifying one or more gene fusions in a biological sample comprising:
one or more computers and one or more storage devices storing instructions that are operable, when executed by the one or more computers, to cause the one or more computers to perform operations comprising:
for each of millions of reference sequence locations:
obtaining, by one or more computers, first data that represents a pileup of aligned reads produced using short read sequencing and having a high depth of coverage at the reference sequence location from a read alignment unit;
determining, by one or more computers, whether one or more gene fusion candidates are included within the obtained first data;

based on a determination that one or more gene fusion candidates are included within the obtained first data, (i) removing, by one or more computers, duplicate fusion candidate occurrences resulting from the high depth of coverage at the reference sequence location, and (ii) adding the remaining gene fusion candidates to a filtered set of gene fusion candidates;

for each particular gene fusion candidate of the filtered set of gene fusion candidates:
  generating, by one or more computers, input data for input to a machine learning model, wherein generating the input data comprises extracting feature data to represent the particular gene fusion candidate from data that includes:
    (i) one or more segments of a reference sequence to which the particular gene fusion candidate was aligned by the read alignment unit, and
    (ii) data generated based on output of the read alignment unit, wherein the data generated based on the output of the read alignment unit includes one or more of a variant allele frequency count, a count of unique read alignments, or a MAPQ score;
  providing, by one or more computers, the generated input data as an input to the machine learning model, wherein the machine learning model has been trained using labeled training vectors, each labeled training vector representing a training fusion candidate and comprising (i) one or more segments of a reference sequence to which the training fusion candidate was aligned, and (ii) one or more of a variant allele frequency count, a count of unique read alignments, or a MAPQ scoreto generate output data representing a likelihood that a gene fusion candidate is a valid gene fusion based on the machine learning model processing input data representing (i) one or more segments of a reference sequence to which the particular gene fusion candidate was aligned to by the read alignment unit, and (ii) data generated based on output of the read alignment unit, wherein the data generated based on the output of the read alignment unit includes one or more of a variant allele frequency count, a count of unique read alignments, or a MAPQ score;
  obtaining, by one or more computers, output data generated by the machine learning model based on the machine learning model processing the generated input data; and
  determining, by one or more computers, whether the particular fusion candidate corresponds to a valid gene fusion candidate based on the output data.

15. The system of claim 14,
wherein generating the input data further comprises extracting feature data that includes annotation data describing annotations of the segments of the reference sequence to which the particular gene fusion candidate was aligned to by the read alignment unit; and
wherein the machine learning model has been trained to generate output data representing a likelihood that a gene fusion candidate is a valid gene fusion candidate based on the machine learning model processing input data representing:
  (i) one or more segments of a reference sequence to which the particular gene fusion candidate was aligned to by the read alignment unit,
  (ii) annotation data describing annotations of the segments of the reference sequence to which the particular gene fusion candidate was aligned to by the read alignment unit, and
  (iii) data generated based on output of the read alignment unit.

16. The system of claim 14, wherein determining, by one or more computers, whether one or more gene fusion candidates are included within the obtained first data comprises identifying, by one or more computers, a plurality of split-read alignments.

17. The system of claim 14, wherein determining, by one or more computers, whether one or more gene fusion candidates are included within the obtained first data comprises identifying, by one or more computers, a plurality of discordant read pair alignments.

18. The system of claim 14, wherein the read alignment unit is implemented using a set of one or more processing engines that are configured using hardware logic circuits that have been physically arranged to perform operations, using the hardware logic circuits, to:
  (i) receive data representing a first read,
  (ii) map the data representing the first read to one or more portions of a reference sequence to identify one or more matching reference sequence locations,
  (iii) generate one or more alignment scores corresponding to each of the matching reference sequence locations for the first read,
  (iv) select one or more candidate alignments for the first read based on the one or more alignment scores, and
  (v) output data representing a candidate alignment for the first read.

19. The system of claim 14, wherein the read alignment unit is implemented using a set of one or more processing engines by using one or more central processing units (CPUs) or one or more graphics processing units (GPUs) to execute software instructions that cause the one or more CPUs or one or more GPUS to:
  (i) receive data representing a first read,
  (ii) map the data representing the first read to one or more portions of a reference sequence to identify one or more matching reference sequence locations for the first read,
  (iii) generate one or more alignment scores corresponding to each of the matching reference sequence locations for the first read,
  (iv) select one or more candidate alignments for the first read based on the one or more alignment scores, and
  (v) output data representing a candidate alignment for the first read.

20. The system of claim 14, the operations further comprising:
wherein obtaining, by one or more computers, first data that represents the pileup of aligned reads from a read alignment unit comprises obtaining, by one or more computers, the pileup of aligned reads from a memory device and performing one or more of the operations of claim 11 while the read alignment unit aligns a second pileup of reads that are not yet aligned.

21. The system of claim 14, wherein determining whether the particular fusion candidate corresponds to a valid gene fusion candidate based on the output data comprises:
  determining, by one or more computers, whether the output data satisfies a predetermined threshold; and based on determining that the output data satisfies the predetermined thresholds, determining that the particular fusion candidate corresponds to a valid gene fusion candidate.

22. The system of claim 14, wherein determining whether the particular fusion candidate corresponds to a valid gene fusion candidate based on the output data comprises:
determining, by one or more computers, whether the output data satisfies a predetermined threshold; and
based on determining that the output data does not satisfy the predetermined thresholds, determining that the particular fusion candidate does not correspond to a valid gene fusion candidate.

23. A non-transitory computer-readable medium storing software comprising instructions executable by one or more computers which, upon such execution, cause the one or more computers to perform operations comprising:
for each of millions of reference sequence locations:
obtaining first data that represents pileup of aligned reads produced using short read sequencing and having a high depth of coverage at the reference sequence location from a read alignment unit;
determining whether one or more gene fusion candidates are included within the obtained first data;
based on a determination that one or more gene fusion candidates are included within the obtained first data, (i) removing duplicate fusion candidate occurrences resulting from the high depth of coverage at the reference sequence location, and (ii) adding the remaining gene fusion candidates to a filtered set of gene fusion candidates;
for each particular gene fusion candidate of the filtered set of gene fusion candidates:
generating input data for input to a machine learning model, wherein generating the input data comprises extracting feature data to represent the particular gene fusion candidate from data that includes:
(i) one or more segments of a reference sequence to which the particular gene fusion candidate was aligned by the read alignment unit, and
(ii) data generated based on output of the read alignment unit, wherein the data generated based on the output of the read alignment unit includes one or more of a variant allele frequency count, a count of unique read alignments, or a MAPQ score;
providing the generated input data as an input to the machine learning model, wherein the machine learning model has been trained using labeled training vectors, each labeled training vector representing a training fusion candidate and comprising (i) one or more segments of a reference sequence to which the training fusion candidate was aligned, and (ii) one or more of a variant allele frequency count, a count of unique read alignments, or a MAPQ score to generate output data representing a likelihood that a gene fusion candidate is a valid gene fusion based on the machine learning model processing input data representing (i) one or more segments of a reference sequence to which the particular gene fusion candidate was aligned to by the read alignment unit, and (ii) data generated based on output of the read alignment unit, wherein the data generated based on the output of the read alignment unit includes one or more of a variant allele frequency count, a count of unique read alignments, or a MAPQ score;
obtaining output data generated by the machine learning model based on the machine learning model processing the generated input data; and
determining whether the particular fusion candidate corresponds to a valid gene fusion candidate based on the output data.

24. The computer-readable medium of claim 23,
wherein generating the input data further comprises extracting feature data that includes annotation data describing annotations of the segments of the reference sequence to which the particular gene fusion candidate was aligned to by the read alignment unit; and
wherein the machine learning model has been trained to generate output data representing a likelihood that a gene fusion candidate is a valid gene fusion candidate based on the machine learning model processing input data representing:
(i) one or more segments of a reference sequence to which the particular gene fusion candidate was aligned to by the read alignment unit,
(ii) annotation data describing annotations of the segments of the reference sequence to which the particular gene fusion candidate was aligned to by the read alignment unit, and
(iii) data generated based on output of the read alignment unit.

25. The computer-readable medium of claim 23, wherein determining whether one or more gene fusion candidates are included within the obtained first data comprises identifying, by one or more computers, a plurality of split-read alignments.

26. The computer-readable medium of claim 23, wherein determining whether one or more gene fusion candidates are included within the obtained first data comprises identifying, by one or more computers, a plurality of discordant read pair alignments.

27. The computer-readable medium of claim 23, wherein the read alignment unit is implemented using a set of one or more processing engines that are configured using hardware logic circuits that have been physically arranged to perform operations, using the hardware logic circuits, to:
(i) receive data representing a first read,
(ii) map the data representing the first read to one or more portions of a reference sequence to identify one or more matching reference sequence locations,
(iii) generate one or more alignment scores corresponding to each of the matching reference sequence locations for the first read,
(iv) select one or more candidate alignments for the first read based on the one or more alignment scores, and
(v) output data representing a candidate alignment for the first read.

28. The computer-readable medium of claim 23, wherein the read alignment unit is implemented using a set of one or more processing engines by using one or more central processing units (CPUs) or one or more graphics processing units (GPUs) to execute software instructions that cause the one or more CPUs or one or more GPUS to:
(i) receive data representing a first read,
(ii) map the data representing the first read to one or more portions of a reference sequence to identify one or more matching reference sequence locations for the first read,
(iii) generate one or more alignment scores corresponding to each of the matching reference sequence locations for the first read, (iv) select one or more candidate alignments for the first read based on the one or more alignment scores, and
(v) output data representing a candidate alignment for the first read.

29. The computer-readable medium of claim 23, the operations further comprising:
wherein obtaining first data that represents the pileup of aligned reads from a read alignment unit comprises obtaining the pileup of aligned reads from a memory device and performing one or more of the operations of claim 21 while the read alignment unit aligns a second pileup of reads that are not yet aligned.

30. The computer-readable medium of claim 23, wherein determining whether the particular fusion candidate corresponds to a valid gene fusion candidate based on the output data comprises:
determining whether the output data satisfies a predetermined threshold; and
based on determining that the output data satisfies the predetermined thresholds, determining that the particular fusion candidate corresponds to a valid gene fusion candidate.

31. The computer-readable medium of claim 23, wherein determining whether the particular fusion candidate corresponds to a valid gene fusion candidate based on the output data comprises:
determining whether the output data satisfies a predetermined threshold; and
based on determining that the output data does not satisfy the predetermined thresholds, determining that the particular fusion candidate does not correspond to a valid gene fusion candidate.

* * * * *